United States Patent [19]
Cao et al.

[11] Patent Number: 5,654,397
[45] Date of Patent: Aug. 5, 1997

[54] INTERLEUKIN-1 RECEPTOR-ASSOCIATED PROTEIN KINASE AND ASSAYS

[75] Inventors: Zhaodan Cao, Pacifica; David V. Goeddel, Hillsborough; Glenn E. Croston, San Diego, all of Calif.

[73] Assignee: Tularik, Inc., South San Francisco, Calif.

[21] Appl. No.: 587,889

[22] Filed: Jan. 16, 1996

Related U.S. Application Data

[63] Continuation of Ser. No. 494,006, Jun. 23, 1985.

[51] Int. Cl.$^6$ .......................... C07K 14/00; C07H 21/04; C12Q 1/68

[52] U.S. Cl. .......................... 530/300; 536/23.1; 536/24.3; 435/4; 435/6

[58] Field of Search ................................. 536/23.1, 24.3; 530/300; 435/6, 4

[56] References Cited

PUBLICATIONS

Liu et al., Journal of Biological Chemistry 269(4): 3047–3052 (Jan. 1994).
The New England Biolabs Catalog, p. 97 (1993/94 Edition).
Martin et al., Eur. J. Immunology 24: 1566–1571 (1994).
Cao et al., Science 271:1128–1131 (Feb. 1996).
Croston et al., Journal of Biological Chemistry 270(28): 16514–16517 (Jul. 1995).

*Primary Examiner*—W. Gary Jones
*Assistant Examiner*—Ethan Whisenandt
*Attorney, Agent, or Firm*—Richard Aron Osman

[57] ABSTRACT

The invention relates to human Interleukin-1 Receptor-Associated Protein Kinases (IRAKs), nucleic acids which encode IRAKs and hybridization probes and primers capable of hybridizing with IRAK genes and methods of using the subject compositions; in particular, methods such as IRAK-based in vitro binding assays and phosphorylation assays for screening chemical libraries for lead compounds for pharmacological agents.

7 Claims, No Drawings

INTERLEUKIN-1 RECEPTOR-ASSOCIATED PROTEIN KINASE AND ASSAYS

CROSS-REFERENCE TO RELATED APPLICATION

This application is a continuation application under 35 USC 120 of U.S. Ser. No. 08/494,006 filed 23 Jun. 1985.

INTRODUCTION

1. Field of the Invention

The field of this invention is a human interleukin receptor associated kinase and its use in drug screening.

2. Background

The cytokine interleukin-1 (IL-1) is a key mediator in the inflammatory response (for reviews, see Refs. 1–3). The importance of IL-1 in inflammation has been demonstrated by the ability of the highly specific IL-1 receptor antagonist protein to relieve inflammatory conditions (for review, see Refs. 1, 4). Many of the proinflammatory effects of IL-1, such as the upregulation of cell adhesion molecules on vascular endothelia, are exerted at the level of transcriptional regulation. The transcriptional activation by IL-1 of cell adhesion molecules and other genes involved in the inflammatory response appears to be mediated largely by NF-κB (5–8). In response to IL-1, the NF-κB inhibitory factor IκB is degraded and NF-κB is released from its inactive cytoplasmic state to localize within the nucleus where it binds DNA and activates transcription (9, 10). Elucidation of the IL-1 signal transduction pathway leading to NF-κB activation would provide valuable insight into mechanisms to alleviate inflammation. In particular, components of this pathway would provide valuable targets for automated, cost-effective, high throughput drug screening and hence would have immediate application in a broad range of domestic and international pharmaceutical and biotechnology drug development programs.

Two cell surface IL-1 receptors, type I (IL-1RI) and type II (IL-1RII), have been identified and molecularly cloned (11, 12). Both receptors have a single transmembrane domain, and an IgG-like extracellular domain. The IL-1RII is found predominantly in B-cells, contains a cytoplasmic domain of only 29 amino acids, and may not play a direct role in intracellular signal transduction (for review, see Ref. 13). The human IL-1RI is found on most cell types and contains 552 amino acids in its mature form. Its cytoplasmic domain of 212 amino acids is required for signaling activity (14–17), but has no significant homology with protein kinases or any other mammalian factors involved in signal transduction. The cytoplasmic domain of IL-1RI does share significant sequence homology with the Drosophila transmembrane protein Toll that is involved in dorsal-ventral patterning (18). This homology may be functionally significant since other components of the Drosophila dorsal-ventral patterning pathway, Dorsal and Cactus, are homologous with NF-κB and IκB, respectively (19). Also, mutation of the amino acids that are conserved between IL-1RI and Toll inactivates IL-1RI signaling in T cells (15).

Relevant Literature

Martin et al. (27) report the existence of a mouse IL-1-dependent protein kinase activity co-precipitating with IL-1RI and specific for an endogenous 60 kD substrate. Heguy et al. (15) disclose amino acids conserved in IL-1R and the Drosophila Toll protein that are essential for signal transduction.

SUMMARY OF THE INVENTION

The invention provides methods and compositions relating to a class of Interleukin-1 Receptor type I-Associated Protein Kinases (IRAK). Native full-length human IRAKs migrate in SDS polyacrylamide gel electrophoresis at an apparent molecular weight of approximately 100 kD. The compositions include nucleic acids which encode IRAKs and hybridization probes and primers capable of hybridizing with the IRAK genes.

The invention includes methods for screening chemical libraries for lead compounds for a pharmacological agent useful in the diagnosis or treatment of disease associated an IRAK activity or an IRAK-dependent signal transduction. In one embodiment, the methods involve (1) forming a mixture comprising an IRAK, a natural intracellular IRAK substrate or binding target such as the Interleukin-1 receptor, and a candidate pharmacological agent; (2) incubating the mixture under conditions whereby, but for the presence of said candidate pharmacological agent, said IRAK selectively phosphorylates said substrate or binds said binding target; and (3) detecting the presence or absence of specific phosphorylation of said substrate by said IRAK or phosphorylation or binding of said IRAK to said binding target, wherein the absence of said selective binding indicates that said candidate pharmacological agent is a lead compound for a pharmacological agent capable of disrupting IRAK function.

DETAILED DESCRIPTION OF THE INVENTION

The nucleotide sequence of a natural cDNA encoding human IRAK-1 is shown as SEQUENCE ID NO:1 and the full conceptual translate is shown as SEQUENCE ID NO:2. The IRAKs of the invention include natural derivatives of the IRAK gene and gene product. For example, IRAK-2 is encoded by a derivative of the IRAK-1 cDNA where the coding region encompassing nucleotides 1514–1552 is deleted. Similarly, IRAK-3 is a derivative of IRAK-1 where the coding region encompassing nucleotides 1514–1558 is deleted.

The disclosed IRAKs include incomplete translates and deletion mutants of these cDNA sequences and deletion mutants, which translates or deletion mutants have IRAK-specific function such as the kinase activity described herein or IRAK self-association function. For example, the domain bound by residues 212 (Phe) through 523 (Ala) of SEQUENCE ID NO:2 defines an active kinase domain which may be used, independently or joined to other domains, in the subject methods. Similarly, the domain defined by the N-terminal 120 residues of SEQUENCE ID NO:2 defines an IRAK self-association domain. This domain finds use in methods involving higher order IRAK complexes which provide an important means of IRAK regulation. Hence, this domain may be used independendy as a regulator or IRAK activity, as a reagent in an IRAK complex formation assay, etc.

The claimed IRAK proteins are isolated, partially pure or pure and are typically recombinantly produced. An "isolated"0 protein for example, is unaccompanied by at least some of the material with which it is associated in its natural state and constitutes at least about 0.5%, preferably at least about 2%, and more preferably at least about 5% by weight of the total protein in a given sample; a partially pure protein constitutes at least about 10%, preferably at least about 30%, and more preferably at least about 60% by weight of the total protein in a given sample; and a pure protein constitutes at least about 70%, preferably at least about 90%, and more preferably at least about 95% by weight of the total protein in a given sample. A wide variety of molecular and biochemical methods are available for generating and expressing the subject compositions, see e.g. Molecular Cloning, A Laboratory Manual (Sambrook, et al. Cold Spring Harbor Laboratory), Current Protocols in Molecular Biology (Eds. Aufubel, et al., Greene Publ. Assoc., Wiley-Interscience, New York) or that are otherwise known in the art.

The invention provides IRAK-specific binding agents including substrates, natural intracellular binding targets, etc. and methods of identifying and making such agents, and their use in diagnosis, therapy and pharmaceutical development. For example, IRAK-specific agents are useful in a variety of diagnostic and therapeutic applications, especially where disease or disease prognosis is associated with improper utilization of a pathway involving an IRAK, e.g. IL-1 receptor activation. Novel IRAK-specific binding agents include IRAK-specific antibodies and other natural intracellular binding agents identified with assays such as one- and two-hybrid screens, non-natural intracellular binding agents identified in screens of chemical libraries, etc. Agents of particular interest modulate IRAK function, e.g. IRAK antagonists.

Generally, IRAK-specificity of the binding agent is shown by kinase activity (i.e. the agent demonstrates activity of an IRAK substrate, agonist, antagonist, etc.) or binding equilibrium constants (usually at least about $10^7 M^{-1}$, preferably at least about $10^8 M^{-1}$, more preferably at least about $10^9 M^{-1}$). A wide variety of cell-based and cell-free assays may be used to demonstrate IRAK-specific binding; preferred are rapid in vitro, cell-free assays such as mediating or inhibiting IRAK-protein (e.g. IRAK-IL-1 RI) binding, phosphorylation assays, immunoassays, etc.

The invention also provides nucleic acids encoding the subject proteins, which nucleic acids may be part of IRAK-expression vectors and may be incorporated into recombinant cells for expression and screening, transgenic animals for functional studies (e.g. the efficacy of candidate drugs for disease associated with expression of an IRAK), etc., and nucleic acid hybridization probes and replication/amplification primers having an IRAK cDNA specific sequence contained in SEQUENCE ID NO:1. Nucleic acids encoding IRAKs are isolated from eukaryotic cells, preferably human cells, by screening cDNA libraries with probes or PCR primers derived from the disclosed IRAK cDNAs. In addition, the invention provides IRAK gene homologs sharing sufficient sequence similarity with that of the disclosed IRAK cDNAs to effect hybridization. Such IRAK cDNA homologs are capable of hybridizing to the IRAK-encoding nucleic acid defined by SEQUENCE ID NO:1 under low stringency conditions, e.g. a hybridization buffer comprising 0% formamide in 0.9M saline/0.09M sodium citrate (SSC) buffer at a temperature of 37° C. and remaining bound when subject to washing at 42° C. with the SSC buffer at 37° C.; or 30% formamide in 5×SSPE (0.18M NaCl, 0.01 M NaPO₄, pH7.7, 0.001M EDTA) buffer at a temperature of 42° C. and remaining bound when subject to washing at 42° C. with the 0.2×SSPE. Preferred nucleic acids will hybridize under moderately stringent conditions, e.g. a hybridization buffer comprising 20% formamide in 0.9M saline/0.09M sodium citrate (SSC) buffer at a temperature of 42° C. and remaining bound when subject to washing at 42° C. with 2×SSC buffer at 42° C.; or a hybridization buffer comprising 50% formamide in 5×SSPE buffer at a temperature of 42° C. and remain bound when subject to washing at 42° C. with 0.2×SSPE buffer at 42° C. More preferred nucleic acids encode kinases comprising kinase domains with at least about 25%, preferably at least about 50% pair-wise identity to a disclosed IRAK kinase domain.

The subject nucleic acids are recombinant, meaning they comprise a sequence joined to a nucleotide other than that which it is joined to on a natural chromosome and are often isolated, i.e. constitute at least about 0.5%, preferably at least about 5% by weight of total nucleic acid present in a given fraction. The recombinant nucleic acids may be contained within vectors, cells or organisms. The subject nucleic acids find a wide variety of applications including use as translatable transcripts, hybridization probes, PCR primers, therapeutic nucleic acids, etc.; use in detecting the presence of IRAK genes and gene transcripts, in detecting or amplifying nucleic acids encoding additional IRAK homologs and structural analogs, and in gene therapy applications.

The invention provides efficient methods of identifying pharmacological agents or lead compounds for agents active at the level of an IRAK modulatable cellular function, particularly IRAK mediated IL-1 signal transduction, especially in inflammation. Generally, these screening methods involve assaying for compounds which interfere with an IRAK activity such as kinase activity or IL-1 receptor I binding. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of the formation of a complex comprising an IKAK and one or more natural IRAK intracellular binding targets including substrates. Target indications may include infection, genetic disease, cell growth and regulatory disfunction, such as neoplasia, inflammation, hypersensitivity, etc.

A wide variety of assays for binding agents are provided including labeled in vitro kinase assays, protein-protein binding assays, immunoassays, cell based assays, etc. The IRAK compositions used the methods are usually added in an isolated, partially pure or pure form and are typically recombinantly produced. The IRAK may be part of a fusion product with another peptide or polypeptide, e.g. a polypeptide that is capable of providing or enhancing protein-protein binding, stability under assay conditions (e.g. a tag for detection or anchoring), etc. The assay mixtures comprise a natural intracellular IRAK binding target including substrates, such as the C-terminus IL-1 RI or, in the case of an autophosphorylation assay, the IRAK itself can function as the binding target. An IRAK derived pseudosubstrate may be used or modified (e.g. A to S/T substitutions) to generate effective substrates for use in the subject kinase assays. The use of serine/threonine kinase pseudosubstrate peptides and the generation of substrate peptides therefrom are well known in the art. While native binding targets may be used, it is frequently preferred to use portions (e.g. peptides, nucleic acid fragments) thereof so long as the portion provides binding affinity and avidity to the subject IRAK conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the IRAK specifically binds the cellular binding target, portion or analog. The mixture components can be added in any order that provides for the requisite bindings. Incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the IRAK and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). For kinase assays, binding is detected by a change in the kinase activity of the IRAK.

Detection may be effected in any convenient way. For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

The following experiments and examples are offered by way of illustration and not by way of limitation.

EXPERIMENTAL

Based on its lack of homology with any known mammalian signal transducers, it likely that the intracellular region of IL-1RI interacts with other factors to transduce IL-1 signals. We sought to delineate a receptor domain that interacts with such factors by examining the ability of IL-1RI mutants to activate NF-κB. To measure NF-κB activation we utilized an assay in which expression vectors for IL-1RI mutants were cotransfected with an E-selectin promoter-luciferase reporter plasmid into the human 293 cell line. Stimulation of E-selectin transcription by IL-1 is known to occur primarily through the activation of NF-κB (24, 25). Luciferase activity in transiently transfected 293 cells was determined in the presence or absence of IL-1 stimulation. In the absence of transfected receptor, IL-1 ( 1 ng/ml) induced a low level of transcriptional activation through endogenous IL-1RI. However, a large increase in IL-1 dependent transcriptional activation was observed in cells transiently transfected with wild type IL-1RI. This result demonstrates that the majority of reporter activity in transiently transfected cells is signaled by transfected IL-1RI, and validates the use of this system for the analysis of IL-1RI mutants.

Five different C-terminal truncation mutants of IL-1RI were examined for their ability to activate the E-selectin reporter in response to IL-1. Removal of 20, 25 or 31 amino acids from the C-terminus did not appreciably affect the ability of IL-1RI to activate NF-κB. Deletion of 45 or 75 C-terminal amino acids eliminated the ability of IL-1RI to activate NF-κB. Therefore, the region defined by the −31 and −45 deletions (residues 508–521) includes sequences required for the activation of NF-κB by IL-1. Furthermore, the −45 and −75 deletion mutants behaved as dominant negative mutations and blocked the ability of the endogenous IL-1RI to activate NF-κB.

Since amino acids 508 to 521 of IL-1RI appear necessary for signal transduction, this region was examined more closely by constructing receptors with sets of three amino acids mutated to alanine. These mutants, which include 510–512A, 513–515A, and 518–520A, were analyzed in the NF-κB reporter assay for their ability to activate NF-κB. By this analysis the 510–512A mutant is active, while the 513–515A and 518–520A mutants are inactive. Amino acids 510, 511, and 512 of the IL-1RI are not conserved in Toll, while conserved amino acids are present in both the 513–515 and 518–520 regions. The requirement of these conserved residues for IL-1RI function may indicate that these amino acids directly contact signaling molecules or are critical to overall receptor structure.

We next performed immunoprecipitation experiments to identify IL-1RI-associated signaling molecules. Immunoprecipitation of metabolically $^{35}$S-labeled IL-1RI from transiently transfected 293 cells reveals that the receptor is expressed at high levels and can be specifically immunoprecipitated with polyclonal antisera directed against the IL-1RI extracellular domain. In agreement with previously published results (20), FACS analysis of 293 cells transiently transfected with 1L-1RI indicated that a large percentage (~40%) of the cell population express receptor. The addition of IL-1 to cells prior to cell lysis had no effect on the ability of the antisera to immunoprecipitate IL-1RI.

To determine whether a protein kinase associates with IL-1RI, the receptor was immunoprecipitated from transiently transfected 293 cells and examined by an in vitro kinase assay. An IL-1-inducible protein kinase activity was observed that specifically associated with IL-1RI. We have termed this activity IRAK (IL-1RI Associated-Kinase). The major target of the IRAK in this reaction is an endogenous substrate of approximately 100 kDa. The specificity of the receptor-kinase interaction is supported by the absence of activity in the preimmune precipitate, and by the ability of an IL-1RI-IgG fusion protein to compete away the kinase activity when added to the immunoprecipitation. Kinase activation occurred rapidly, reaching an optimum within two minutes of exposure of cells to IL-1, suggesting that activation of the kinase occurs proximally to the IL-1 receptor.

If IRAK is involved in NF-κB activation, then the activity of the kinase in immunoprecipitates of mutated receptor should correlate with in vivo activation of the E-selectin reporter by mutated receptors. The C-terminal deletions mutants of IL-1RI were transiently expressed in 293 cells, receptor was immunoprecipitated, and examined for associated IL-1 inducible kinase activity. In the absence of transfected receptor, 293 cells display low but detectable levels of IRAK activity. All three C-terminal deletion mutants (−20, −25, −31) that can activate NF-κB display associated kinase activity that is indistinguishable from that associated with intact IL-1RI. IRAK activity does not coprecipitate with the −45 deletion mutant that was unable to activate NF-κB. Thus, there is a direct correlation between the association of active IRAK with IL-1RI and the ability of IL-1 to activate NF-κB.

To further examine the connection between NF-κB activation and IRAK kinase activity, the triple alanine scan mutants of IL-1RI were examined by the coimmunoprecipitation assay following transfection into 293 cells. IRAK activity was observed with the 510–512A mutant, but not with the 513–515 Ala or 518–520 Ala mutants. Once again there was a direct correlation between the ability of an IL-1RI mutant to interact with IRAK and to induce NF-κB activation.

In order to purify pp100, we stably transfected 293 cells with IL-1RI expression plasmid. The 293/IL-1RI cells express IL-1RI at a level at least two orders of magnitude greater than that of parental 293 cells as shown by FACS analyses. The cells were gown in suspension and treated briefly with IL-1 before harvest and extract preparation. pp100 was purified from extracts prepared from 100 liters of cells by a large scale immunoprecipitation using rabbit antibodies to the extracellular domain of IL-1RI. To follow pp100, immunoprecipitants were subjected to an in vitro kinase reaction in the presence of $\gamma^{32}P$-ATP. pp100 eluted from the IL-1RI immunocomplex was further purified by Q sepharose column chromatography. Protein fractions containing radiolabeled pp100 were subjected to two-dimensional gel electrophoresis and blotted to polyvinylidene difluoride (PVDF) membrane. pp100 (about 0.4 µg) was identified by autoradiography and digested with lysine-C and trypsin. The resulting peptides were fractionated by capillary high-performance liquid chromatography. Amino acid sequences of 10 polypeptides were obtained, which were used to design degenerate oligonucleotides as primers for polymerase chain reaction (PCR). A DNA fragment of 356 nucleotides was amplified from cDNA prepared using mRNA from 293 cells. This DNA fragment encodes the peptide used to design the PCR primers as well as three other sequenced peptides. Using this DNA fragment as a probe, we isolated corresponding cDNA clones from a human teratocarcinoma cDNA library. The longest clone obtained is 3.5 kilobase pair in length (SEQUENCE ID NO: 1) and encodes a protein of 699 amino acids (SEQUENCE ID NO:2). An in-frame stop codon was located 36 nucleotides upstream from the first methionine, indicating that the clone encodes a full length protein.

Sequence analysis of the protein revealed a region similar to the catalytic domain of kinases. Eleven subdomains and 15 invariable amino acids indicative of a protein kinase are present. Search of the NCBI BLAST database with the kinase domain sequence revealed similarity between pp100 and several serine/threonine kinases. The kinase of animal origin that shared highest sequence similarity with pp100 is drosophila Pelle which is 33% identical in the 298 amino acid kinase domain. The research also revealed homology between pp100 and few plant kinases of unknown functions and the plant Tpo gene which confers resistance to bacteria Pseudomonas syringae pv. tomato in Tomato.

METHODS I: IDENTIFICATION OF IRAK ACTIVITY

Plasmid Construction and Antiserum Preparation

The human IL-1RI cDNA was cloned into pRK5 (20) to give the plasmid pRK-IL-1RI in which expression is under the control of the cytomegalovirus immediate early promoter-enhancer. Expression plasmids for the C-terminal deletion mutants of IL-1 receptor were generated from pRK-IL-1RI by introducing stop codons into the IL-1RI coding region by polymerase chain reaction (PCR). The internal triple mutants were made by a procedure involving two rounds of PCR. The first round of PCR generated overlapping fragments with the corresponding mutations in the center of the overlapped region. The two fragments were joined by a second round of PCR. The sequences of all constructs were confirmed by DNA sequencing. To prepare antiserum to the extracellular domain of the IL-1RI, a fusion protein consisting of the mature IL-1RI extracellular domain fused to human IgG as described (22), was expressed transiently in 293 cells. Cell culture medium containing the chimeric protein was harvested on 3 and 7 days after transfection. The IL-1RI-IgG fusion protein was purified by protein A-agarose chromatography and used to immunize rabbits by BAbCo (Richmond, Calif.).

Cell culture, transfection, cell extract preparation and metabolic labeling

Human embryonic kidney 293 cells were grown in DMEM medium supplemented with 10% fetal calf serum, 100 mg/ml penicillin G and 100 mg/ml streptomycin (Gibco). To assay receptor function, cells were seeded in 6-well dishes at 30–50% confluence. Transfections were carried out the following day with the various expression plasmids by the calcium phosphate precipitation method (23). 36 hours later, human recombinant IL-1β (Genentech) was added to the medium at final concentration of 1 ng/ml. The cells were harvested 6 hours later and assayed for luciferase activity using Promega reagents. β-galactosidase activity was determined using chemiluminescent reagents (Tropix, Inc.) and used to normalize luciferase activities. Extracts for immunoprecipitations and in vitro phosphorylation assays were prepared as follows: 293 cells were seeded at 50% density in 100 mm plates and transfected with IL-1RI expression plasmids on the following day. 40 to 48 hours later, IL-1 (20 ng/ml) was added to the media. After incubation at 37° C. for the indicated times, media was removed and the plates were chilled on ice immediately. The cells were washed twice with 5 ml of ice-cold phosphate buffered saline (PBS) and scraped off the plates in 5 ml of PBS containing 1 mM EDTA. Cells were pelleted by 1200 x g centrifugation for 3 minutes and suspended in 1 ml of lysis buffer (5.0 mM HEPES pH 7.6, 250 mM NaCl, 1 mM dithiothreitol (DTT), 1 mM EDTA, 0.1% TWEEN-20® detergent, 10% (v/v) glycerol, 10 mM b-glycerophosphate, 5 mM p-nitrophenyl phosphate, 1 mM Na orthovanadate, 1 mM benzamidine, 0.4 mM phenylmethylsulfonyl fluoride, 1 mM Na metabisulfite, 10 ug/ml leupeptin and 10 ug/ml aprotinin). After incubation on ice for 20 minutes, the cell debris was pelleted by a 20 minute centrifugation in a microcentrifuge and the supernatants were collected and stored at −70° C. For metabolic labelling, 293 cells were seeded in 150 mm plates and grown to near confluence. The cells were washed twice with 25° C. PBS and incubated with DMEM lacking cysteine and methionine at 37° C. for 40 minutes before addition of 700 uCi of $^{35}S$ cell labelling mix (Amersham). Four hours later, the medium was removed and cells were washed twice with PBS and extracts were prepared as described above.

Immunoprecipitation and in vitro kinase assays

For immunoprecipitations, 1 ml of celluar extrxact was incubated with 20 ml of protein A-agarose slurry (50% v/v) in lysis buffer at 4° C. for 2 hours. Protein A beads were pelleted by centrifugation in a microcentrifuge for 10 seconds and 1 ml of rabbit antiserum or preimmune serum was incubated with the precleared supernatant at 4° C. for 2–3 hours. The reactions were mixed with 20 ul of the protein A-agarose slurry and incubated for an additional 1 hour. Protein A beads were collected by centrifugation in a microcentrifuge for 10 seconds, and washed 5 times with 1 ml of lysis buffer. The beads were then suspended in 20 ul of kinase buffer containing 20 mM Tris-HCl pH 7.6, 20 mM $MgCl_2$, 20 mM β-glycerophosphate, 20 mM p-nitrophenyl phosphate, 1 mM Na orthovanadate, 1 mM benzamidine, 0.4 mM PMSF, 1 mM Na metabisulfite, 2 uM cold ATP and 10 uCi [$^{32}$P]γ-ATP. The kinase reactions were allowed to proceed at 30° C. for 30 minutes and terminated with 20 ml of SDS sample buffer. After boiling for 3–5 minutes, 20 ml reaction aliquots were separated by 8% SDS-PAGE. Radio-labeled proteins were visualized by autoradiography.

METHODS II. PURIFICATION AND CLONING OF IRAK

Cell Culture:

293 cells were cultured in Dulbeco's Modification of Eagle's Medium with 4.5 gram/ml glucose and L-glutamine (Mediatech) supplemented with 10% fetal bovine serum, 100 ug/ml streptomycin and 100 ug/ml penicillin. To make 293 cells overproducing the human IL-1RI, 293 cells were seeded on 100 mm plates at 30% density and were transfected on the following day with 10 mg IL-1RI expression plasmid (supra) and 1 mg pNeo by calcium phosphate precipitation. Stably transfected cells were selected with culture medium containing 500 μg/ml of G418 (Gibco). Ten individual colonies were cloned and expanded. The expression IL-RI on the cell surface was monitored by FACS using antibody to the extracellular domain of the IL-1RI. Four clones which showed the desirable IL-1RI expression and growth behavior were transferred to suspension culture in $CO_2$-independent Minimum Essential Medium (MEM, Mediatech) supplemented 10% fetal bovine serum, 4.5 g/ml glucose, 1 mM sodium pyruvate (Gibco), 100 ug/ml streptomycin and 100 ug/ml penicillin.

Extract Preparation:

Cells from suspension culture (100 liters) were pelleted in a Sorvall CS-3 rotor at 2500 RPM for 5 minutes and re-suspended in 5 liters of pre-warmed serum-free MEM medium. The cells were incubated with 200 ng/ml recombinant human IL-1β (Genentech) at 37° C. for 3 minutes and pelleted by centrifugation at 4° C. All of the following steps were performed at 4° C. The cells were suspended in 5 pelleted-cell-volumes of buffer containing 50 mM Hepes pH 7.9, 250 mM NaCl, 5 mM dithiothreitol (DTT), 1 mM EDTA, 0.1% NP-40® detergent, 10% (v/v)glycerol, 20 mM b glycerophosphate, 5 mM p-nitrophenyl phosphate, 1 mM Na orthovanatate, 1 mM benzamidine, 0.4 mM phenylmethylsulfonyl fluoride (PMSF), 1 mM Na metabisulfite, 10 ug/ml leupeptin and 10 ug/ml aprotinin. After incubation on ice for 30 minutes with occasional rocking, the cell lysate was centrifuged in a Sorvall H6000A rotor at 4000 RMP for 10 minutes. The supernatants were collected and centrifuged in a Beckman 45 TI rotor at 40,000 RPM for 2 hours. The supernatants were aliquoted and stored at −70° C.

Purification of pp110:

The extracts were thawed and spun in a Beckman 45 TI at 40,000 RPM for 2 hours. The supernatants were incubated with 40 mg of rabbit IgG against the extracellular domain of the IL-1R at 4° C. for 2 hours with rocking. 25 ml of protein A sepharose CL4B (Pharmacia) were mixed with the extracts and the incubation continued for another 2 hours. The protein A beads were collected in a column and washed with 250 ml of washing buffer #1 containing 50 mM Hepes pH 7.9, 250 mM NaCl, 5 mM dithiothreitol (DTT), 1 mM EDTA, 0.1% NP-40® detergent, 20 mM β glycerophosphate, 1 mM Na orthovanatate, 1 mM benzamidine, 0.4 mM phenylmethylsulfonyl fluoride (PMSF), 1 mM Na metabisulfite. The beads were then suspended in 50 ml kinase buffer containing 20 mM Tris-HCl pH 7.6, 20 mM $MgCl_2$, 20 mM β glycerophosphate, 20 mM p-nitrophenylphosphate, 1 mM EDTA, 1 mM Na orthovanadate, 1 mM benzamidine, 0.4 mM PMSF, 1 mM Na metabisulfite, 5 mM cold ATP and 100 mCi [$^{72}$P]g -ATP and incubated at 30° C. for 15 minutes. The kinase reaction was chased with 100 mM of unlabeled ATP for an additional 15 minutes. Protein A beads were collected in an empty column and washed with 150 ml of washing buffer #2 containing 150 ml of buffer consisted of 50 mM Hepes, pH 7.9, 1M NaCl, 5 mM DTT, 1 mM EDTA and 0.1% NP40, then 150 ml of washing buffer #3 consisting of 50 mM Hepes, pH 7.9, 100 mM NaCl, 2M urea, 5 mM DTT, 1 mM EDTA and 0.1% NP40. The proteins were then eluted with 50 ml of elution buffer containg 50 mM Hepes, pH 7.9, 100 mM NaCl, 5 mM DTT, 1 mM EDTA, 0.1% NP- 40 and 7M urea at 4° C. overnight with rocking. The eluted materials were loaded on a 0.5 ml Q Sepharose column equilibrated in the elution buffer. The column was washed extensively with the elution buffer before bound proteins were eluted with buffer containing 0.5M NaCl. The high salt eluate was concentrated in a Centricon 50 (Microcon) to 50 μl, diluted with 1 ml isoelectric focusing sample buffer (O'Farrell (1975) J. Biol Chem), concentrated down again to 50 μl. The sample was then subjected to two-dimensional gel electrophoresis.

Two-dimensional gel electrophoresis and micro peptide sequencing:

Isoelectric focusing was used as the first dimensional separation. The preparation and running conditions were described previously. The pH gradient was created with ampholines pH 5.0–7.0 and pH 3.5–9.5 blended at a radio of 1:1. 7% acrylamide SDS gel electrophoresis was used as second dimension separation. After the electrophoresis, the proteins were transferred to a polyvinylidenedifluoride membrane (Milipore) and stained with Coomassie blue R-250 in 40% methanol and 10% acetic acid for 30 seconds, followed by a 5 minute de-staining in 40% methanol and 10% acetic acid. The area of membrane containing the pp100 substrate indicated by autoradiography was exercised and subjected to peptidase digestion and micro-peptide-sequencing as described (Hou et al. (1994) Science 265, 1701–1706).

Parenthetical References (1) Dinarello (1991) *Blood* 77: 1627–1652; (2) Dinarello and Wolff (1993) *New England J. Med.* 328:106–113; (3) Dinarello (1994) *FASEB J.* 8:1314–1325; (4) Dinarello (1993) *Immunol. Today* 14:260–264; (5) Shirakawa and Mizel (1989) *Molec. Cell Biol.* 9:2424–2430; (6) Osborn et al., (1989) *Proc. Natl. Acad. Sci. USA* 86:2336–2340; (7) Krasnow et al., (1991) *Cytokine* 3:372–379; (8) Collins et al., (1993) *Trends Cardiovasc. Med.* 3:92–97; (9) Liou and Baltimore (1993) *Curr. Opin. in Cell Biol.* 5:477–487; (10) Beg et al., (1993) *Mol. Cell. Bid.* 13:3301–3310; (11) Sims et al., (1988) *Science* 241:585–589; (12) McMahan et al., (1991) *EMBO J.* 10:2821–2832; (13) Colotta et al., (1994) *Immunol. Today* 15:562–566; (14) Curtis et al., (1989) *Proc. Natl. Acad. Sci. USA* 86:3045–3049; (15) Heguy et al., (1992) *J. Biol. Chem.* 267:2605–2609; (16) Kuno et al., (1993) *J. Biol. Chem.* 268:13510–13518; (17) Leung et al., (1994) *J. Biol. Chem.* 269:1579–1582; (18) Hashimoto et al., (1988) *Cell* 52:269–279; (19) Wasserman (1993) *Molec. Biol. of the Cell* 4:767–771; (20) Schall et al., (1990) *Cell* 61:361–370; (21) Schindler and Baichwal (1994) *Mol. Cell. Biol.* 5820–5831; (22) Pitti et al., (1994) *Mol. Immunol.* 17:1345–135; (23) Ausubel et al., (1994) *Current Protocols in Molecular Biology* Greene Publishing Associates/Wiley & Sons, New York; (24) Whelan et al., (1991) *Nucleic Acids Res.* 19:2645–2653; (25) Montgomery et al., (1991) *Proc. Natl. Acad. Sci. USA* 88:6523–6527; (26) Stylianou et al., (1992) *J. Biol. Chem.* 267:15836–15841; (27) Martin et al., (1994) *Eur. J. Immunol.* 24:1566–1571; and (28) Freshney et al., (1994) *Cell* 78:1039–1049.

EXAMPLES

1. Protocol for IRAK autophosphorylation assay.

A. Reagents:

Neutralite Avidin: 20 µg/ml in PBS.

IRAK: $10^{-8}$–$10^{-5}$M biotinylated IRAK-1 at 20 µg/ml in PBS.

Blocking buffer: 5% BSA, 0.5% TWEEN-20® detergent in PBS; 1 hour at room temperature.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

[$^{32}$P]γ-ATP 10× stock 2×$10^{-5}$M cold ATP with 100 µCi [$^{32}$P]γ-ATP. Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

B. Preparation of assay plates:

Coat with 120 µl of stock N Avidin per well overnight at 4° C.

Wash 2 times with 200 µl PBS.

Block with 150 µl of blocking buffer.

Wash 2 times with 200 µl PBS.

C. Assay:

Add 40 µl assay buffer/well.

Add 40 µl biotinylated IRAK (0.1–10 pmoles/40 ul in assay buffer)

Add 10 µl compound or extract.

Add 10 µl [$^{32}$P]γ-ATP 10× stock.

Shake at 25° C. for 15 minutes.

Incubate additional 45 minutes at 25 ° C.

Stop the reaction by washing 4 times with 200 µl PBS.

Add 150 µl scintillation cocktail.

Count in Topcount.

Controls for all assays (located on each plate):

a. Non-specific binding b. cold ATP at 80% inhibition.

2. Protocol for IRAK—IL1RI complex formation assay,

A. Reagents:

Neutralite Avidin: 20 µg/ml in PBS.

Blocking buffer: 5% BSA, 0.5% TWEEN-20® detergent in PBS; 1 hour at room temperature.

Assay Buffer: 100 mM KCl, 20 mM HEPES pH 7.6, 0.25 mM EDTA, 1% glycerol, 0.5% NP-40, 50 mM β-mercaptoethanol, 1 mg/ml BSA, cocktail of protease inhibitors.

$^{33}$P IRAK 10× stock: $10^{-8}$–$10^{-6}$M "cold" IRAK supplemented with 200,000–250,000 cpm of labeled IRAK (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

IL-1RI: $10^{-8}$–$10^{-5}$M biotinylated IL-1RI intracellular domain (residues 327–527) in PBS.

B. Preparation of assay plates:

Coat with 120 µl of stock N-Avidin per well overnight at 4° C.

Wash 2 times with 200 µl PBS.

Block with 150 µl of blocking buffer.

Wash 2 times with 200 µl PBS.

C. Assay:

Add 40 µl assay buffer/well.

Add 10 µl compound or extract.

Add 10 µl $^{33}$P-IRAK (20,000–25,000 cpm/0.1–10 pmoles/well=$10^{-9}$–$10^{-7}$M final concentration).

Shake at 25° C. for 15 minutes.

Incubate additional 45 minutes at 25 ° C.

Add 40 µl biotinylated IL-1RI intracellular domain (0.1–10 pmoles/40 ul in assay buffer)

Incubate 1 hour at room temperature.

Stop the reaction by washing 4 times with 200 µl PBS.

Add 150 µl scintillation cocktail.

Count in Topcount.

D. Controls for all assays (located on each plate):

a. Non-specific binding b. Soluble (non-biotinylated IL-1RI intracellular domain) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated human Interleukin-1 Receptor-Associated Protein Kinase (IRAK) comprising at least one of SEQ ID NO:2, residues 1–120 and SEQ ID NO:2, residues 212–523.

2. An isolated human Interleukin-1 Receptor-Associated Protein Kinase (IRAK) comprising a kinase domain, said kinase domain comprising the amino acid sequence of SEQ ID NO:2, residues 212–523.

3. An isolated nucleic acid encoding a human Interleukin-1 Receptor-Associated Protein Kinase (IRAK) kinase domain according to claim 1.

4. A method of identifying lead compounds for a pharmacological agent useful in the diagnosis or treatment of disease associated with Interleukin-1 signal transduction, said method comprising the steps of:
   forming a mixture comprising:
   a human IRAK according to claim 1,
   a natural intracellular IRAK binding target, wherein said binding target is capable of specifically binding said IRAK, and
   a candidate pharmacological agent;
   incubating said mixture under conditions whereby, but for the presence of said candidate pharmacological agent, said IRAK selectively binds said binding target;
   detecting the presence or absence of specific binding of said IRAK to said binding target,
   wherein the absence of said selective binding indicates that said candidate pharmacological agent is a lead compound for a pharmacological agent capable of disrupting IRAK-dependent signal transduction.

5. A method according to claim 4, wherein said IRAK binding target comprises an intracellular fragment of the Interleukin-1 receptor.

6. A method of identifying lead compounds for a pharmacological agent useful in the diagnosis or treatment of disease associated with Interleukin-1 Receptor Associated Protein Kinase activity, said method comprising the steps of:
   forming a mixture comprising:
   a human IRAK according to claim 1,
   a natural intracellular IRAK substrate, wherein said IRAK is capable of specifically phosphorylating said substrate, and
   a candidate pharmacological agent;
   incubating said mixture under conditions whereby, but for the presence of said candidate pharmacological agent, said IRAK selectively phosphorylates said substrate;
   detecting the presence or absence of specific phosphorylation of said substrate by said IRAK,
   wherein the absence of said phosphorylation indicates that said candidate pharmacological agent is a lead compound for a pharmacological agent capable of disrupting IRAK activity.

7. A method according to claim 6 wherein said IRAK substrate is said IRAK.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:

( A ) LENGTH: 3590 base pairs (B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:1:

```
CGCGGACCCG GCCGGCCCAG GCCCGCGCCC GCCGCGGCCC TGAGAGGCCC CGGCAGGTCC     60
CGGCCCGGCG GCGGCAGCCA TGGCCGGGGG GCCGGGCCCG GGGGAGCCCG CAGCCCCGG    120
CGCCCAGCAC TTCTTGTACG AGGTGCCGCC CTGGGTCATG TGCCGCTTCT ACAAAGTGAT   180
GGACGCCCTG GAGCCGCCG ACTGGTGCCA GTTCGCCGCC CTGATCGTGC GCGACCAGAC    240
CGAGCTGCGG CTGTGCGAGC GCTCCGGGCA GCGCACGGCC AGCGTCCTGT GGCCCTGGAT   300
CAACCGCAAC GCCCGTGTGG CCGACCTCGT GCACATCCTC ACGCACCTGC AGCTGCTCCG   360
TGCGCGGGAC ATCATCACAG CCTGGCACCC TCCCGCCCCG CTTCCGTCCC CAGGCACCAC   420
TGCCCCGAGG CCCAGCAGCA TCCCTGCACC CGCCGAGGCC GAGGCCTGGA GCCCCCGGAA   480
GTTGCCATCC TCAGCCTCCA CCTTCCTCTC CCCAGCTTTT CCAGGCTCCC AGACCCATTC   540
AGGGCCTGAG CTCGGCCTGG TTCCAAGCCC TGCTTCCCTG TGGCCTCCAC CGCCATCTCC   600
AGCCCCTTCT TCTACCAAGC CAGGCCCAGA GAGCTCAGTG TCCTCCTGC AGGGAGCCCG    660
CCCCTCTCCG TTTTGCTGGC CCCTCTGTGA GATTTCCCGG GGCACCCACA ACTTCTCGGA   720
GGAGCTCAAG ATCGGGGAGG GTGGCTTTGG GTGCGTGTAC CGGGCGGTGA TGAGGAACAC   780
GGTGTATGCT GTGAAGAGGC TGAAGGAGAA CGCTGACCTG GAGTGGACTG CAGTGAAGCA   840
GAGCTTCCTG ACCGAGGTGG AGCAGCTGTC CAGGTTTCGT CACCCAAACA TTGTGGACTT   900
TGCTGGCTAC TGTGCTCAGA ACGGCTTCTA CTGCCTGGTG TACGGCTTCC TGCCCAACGG   960
CTCCCTGGAG GACCGTCTCC ACTGCCAGAC CCAGGCCTGC CCACCTCTCT CCTGGCCTCA  1020
GCGACTGGAC ATCCTTCTGG GTACAGCCCG GGCAATTCAG TTTCTACATC AGGACAGCCC  1080
CAGCCTCATC CATGGAGACA TCAAGAGTTC CAACGTCCTT CTGGATGAGA GGCTGACACC  1140
CAAGCTGGGA GACTTTGGCC TGGCCCGGTT CAGCCGCTTT GCCGGGTCCA GCCCCAGCCA  1200
GAGCAGCATG GTGGCCCGGA CACAGACAGT GCGGGGCACC CTGGCCTACC TGCCCGAGGA  1260
GTACATCAAG ACGGGAAGGC TGGCTGTGGA CACGGACACC TTCAGCTTTG GGGTGGTAGT  1320
GCTAGAGACC TTGGCTGGTC AGAGGGCTGT GAAGACGCAC GGTGCCAGGA CCAAGTATCT  1380
GAAAGACCTG GTGGAAGAGG AGGCTGAGGA GGCTGGAGTG GCTTTGAGAA GCACCCAGAG  1440
CACACTGCAA GCAGGTCTGG CTGCAGATGC CTGGGCTGCT CCCATCGCCA TGCAGATCTA  1500
CAAGAAGCAC CTGGACCCCA GGCCCGGGCC CTGCCCACCT GAGCTGGGCC TGGGCCTGGG  1560
CCAGCTGGCC TGCTGCTGCC TGCACCGCCG GCCAAAAGG AGGCCTCCTA TGACCCAGGT  1620
GTACGAGAGG CTAGAGAAGC TGCAGGCAGT GGTGGCGGGG GTGCCCGGGC ATTTGGAGGC  1680
CGCCAGCTGC ATCCCCCTT CCCCGCAGGA GAACTCCTAC GTGTCCAGCA CTGGCAGAGC  1740
CCACAGTGGG GCTGCTCCAT GGCAGCCCCT GGCAGCGCCA TCAGGAGCCA GTGCCCAGGC  1800
AGCAGAGCAG CTGCAGAGAG GCCCCAACCA GCCCGTGGAG AGTGACGAGA GCCTAGGCGG  1860
CCTCTCTGCT GCCCTGCGCT CCTGGCACTT GACTCCAAGC TGCCCTCTGG ACCCAGCACC  1920
CCTCAGGGAG GCCGGCTGTC CTCAGGGGA CACGGCAGGA GAATCGAGCT GGGGGAGTGG   1980
CCCAGGATCC CGGCCCACAG CCGTGGAAGG ACTGGCCCTT GGCAGCTCTG CATCATCGTC  2040
GTCAGAGCCA CCGCAGATTA TCATCAACCC TGCCCGACAG AAGATGGTCC AGAAGCTGGC  2100
CCTGTACGAG GATGGGGCCC TGGACAGCCT GCAGCTGCTG TCGTCCAGCT CCCTCCCAGG  2160
```

-continued

| | | | | | |
|---|---|---|---|---|---|
| CTTGGGCCTG | GAACAGGACA | GGCAGGGGCC | CGAAGAAAGT | GATGAATTTC | AGAGCTGATG | 2220 |
| TGTTCACCTG | GGCAGATCCC | CCAAATCCGG | AAGTCAAAGT | TCTCATGGTC | AGAAGTTCTC | 2280 |
| ATGGTGCACG | AGTCCTCAGC | ACTCTGCCGG | CAGTGGGGGT | GGGGCCCAT | GCCCGCGGGG | 2340 |
| GAGAGAAGGA | GGTGGCCCTG | CTGTTCTAGG | CTCTGTGGGC | ATAGGCAGGC | AGAGTGGAAC | 2400 |
| CCTGCCTCCA | TGCCAGCATC | TGGGGGCAAG | GAAGGCTGGC | ATCATCCAGT | GAGGAGGCTG | 2460 |
| GCGCATGTTG | GGAGGCTGCT | GGCTGCACAG | ACCCGTGAGG | GGAGGAGAGG | GGCTGCTGTG | 2520 |
| CAGGGGTGTG | GAGTAGGGAG | CTGGCTCCCC | TGAGAGCCAT | GCAGGGCGTC | TGCAGCCCAG | 2580 |
| GCCTCTGGCA | GCAGCTCTTT | GCCCATCTCT | TTGGACAGTG | GCCACCCTGC | ACAATGGGGC | 2640 |
| CGACGAGGCC | TAGGGCCCTC | CTACCTGCTT | ACAATTTGGA | AAAGTGTGGC | CGGGTGCGGT | 2700 |
| GGCTCACGCC | TGTAATCCCA | GCACTTTGGG | AGGCCAAGGC | AGGAGGATCG | CTGGAGCCCA | 2760 |
| GTAGGTCAAG | ACCAGCCAGG | GCAACATGAT | GAGACCCTGT | CTCTGCCAAA | AAATTTTTTA | 2820 |
| AACTATTAGC | CTGGCGTGGT | AGCGCACGCC | TGTGGTCCCA | GCTGCTGGGG | AGGCTGAAGT | 2880 |
| AGGAGGATCA | TTTATGCTTG | GGAGGTCGAG | GCTGCAGTGA | GTCATGATTG | TATGACTGCA | 2940 |
| CTCCAGCCTG | GGTGACAGAG | CAAGACCCTG | TTTCAAAAAG | AAAAACCCTG | GAAAAGTGA | 3000 |
| AGTATGGCTG | TAAGTCTCAT | GGTTCAGTCC | TAGCAAGAAG | CGAGAATTCT | GAGATCCTCC | 3060 |
| AGAAAGTCGA | GCAGCACCCA | CCTCCAACCT | CGGGCCAGTG | TCTTCAGGCT | TTACTGGGGA | 3120 |
| CCTGCGAGCT | GGCCTAATGT | GGTGGCCTGC | AAGCCAGGCC | ATCCCTGGGC | GCCACAGACG | 3180 |
| AGCTCCGAGC | CAGGTCAGGC | TTCGGAGGCC | ACAAGCTCAG | CCTCAGGCCC | AGGCACTGAT | 3240 |
| TGTGGCAGAG | GGGCCACTAC | CCAAGGTCTA | GCTAGGCCCA | AGACCTAGTT | ACCCAGACAG | 3300 |
| TGAGAAGCCC | CTGGAAGGCA | GAAAAGTTGG | GAGCATGGCA | GACAGGGAAG | GGAAACATTT | 3360 |
| TCAGGGAAAA | GACATGTATC | ACATGTCTTC | AGAAGCAAGT | CAGGTTTCAT | GTAACCGAGT | 3420 |
| GTCCTCTTGC | GTGTCCCAAA | GTAGCCCAGG | GCTGTAGCAC | AGGCTTCACA | GTGATTTTGT | 3480 |
| GTTCAGCCGT | GAGTCACACT | ACATGCCCCC | GTGAAGCTGG | GCATTGGTGA | CGTCCAGGTT | 3540 |
| GTCCTTGAGT | AATAAAAACG | TATGTTCCCT | AAAAAAAAAA | AAAGGAATTC | | 3590 |

( 2 ) INFORMATION FOR SEQ ID NO:2:

( i ) SEQUENCE CHARACTERISTICS:
( A ) LENGTH: 712 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

```
Met Ala Gly Gly Pro Gly Pro Gly Glu Pro Ala Ala Pro Gly Ala Gln
 1               5                  10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
```

-continued

|     |     |     |     |     | 100 |     |     |     |     | 105 |     |     |     |     | 110 |     |     |
|---|---|---|---|---|---|---|---|---|---|---|---|---|---|---|---|---|---|

```
          100                     105                     110
Thr Thr Ala Pro Arg Pro Ser Ser Ile Pro Ala Pro Ala Glu Ala Glu
        115                 120                 125
Ala Trp Ser Pro Arg Lys Leu Pro Ser Ser Ala Ser Thr Phe Leu Ser
        130             135             140
Pro Ala Phe Pro Gly Ser Gln Thr His Ser Gly Pro Glu Leu Gly Leu
145                 150                 155                 160
Val Pro Ser Pro Ala Ser Leu Trp Pro Pro Pro Ser Pro Ala Pro
                165             170             175
Ser Ser Thr Lys Pro Gly Pro Glu Ser Ser Val Ser Leu Leu Gln Gly
            180             185                 190
Ala Arg Pro Ser Pro Phe Cys Trp Pro Leu Cys Glu Ile Ser Arg Gly
        195             200             205
Thr His Asn Phe Ser Glu Glu Leu Lys Ile Gly Glu Gly Gly Phe Gly
        210             215             220
Cys Val Tyr Arg Ala Val Met Arg Asn Thr Val Tyr Ala Val Lys Arg
225             230             235             240
Leu Lys Glu Asn Ala Asp Leu Glu Trp Thr Ala Val Lys Gln Ser Phe
                245             250             255
Leu Thr Glu Val Glu Gln Leu Ser Arg Phe Arg His Pro Asn Ile Val
            260             265             270
Asp Phe Ala Gly Tyr Cys Ala Gln Asn Gly Phe Tyr Cys Leu Val Tyr
        275             280             285
Gly Phe Leu Pro Asn Gly Ser Leu Glu Asp Arg Leu His Cys Gln Thr
        290             295             300
Gln Ala Cys Pro Pro Leu Ser Trp Pro Gln Arg Leu Asp Ile Leu Leu
305             310             315             320
Gly Thr Ala Arg Ala Ile Gln Phe Leu His Gln Asp Ser Pro Ser Leu
                325             330             335
Ile His Gly Asp Ile Lys Ser Ser Asn Val Leu Leu Asp Glu Arg Leu
            340             345             350
Thr Pro Lys Leu Gly Asp Phe Gly Leu Ala Arg Phe Ser Arg Phe Ala
        355             360             365
Gly Ser Ser Pro Ser Gln Ser Ser Met Val Ala Arg Thr Gln Thr Val
        370             375             380
Arg Gly Thr Leu Ala Tyr Leu Pro Glu Glu Tyr Ile Lys Thr Gly Arg
385             390             395             400
Leu Ala Val Asp Thr Asp Thr Phe Ser Phe Gly Val Val Val Leu Glu
                405             410             415
Thr Leu Ala Gly Gln Arg Ala Val Lys Thr His Gly Ala Arg Thr Lys
            420             425             430
Tyr Leu Lys Asp Leu Val Glu Glu Ala Glu Ala Gly Val Ala
        435             440             445
Leu Arg Ser Thr Gln Ser Thr Leu Gln Ala Gly Leu Ala Ala Asp Ala
        450             455             460
Trp Ala Ala Pro Ile Ala Met Gln Ile Tyr Lys Lys His Leu Asp Pro
465             470             475             480
Arg Pro Gly Pro Cys Pro Pro Glu Leu Gly Leu Gly Leu Gly Gln Leu
                485             490             495
Ala Cys Cys Cys Leu His Arg Arg Ala Lys Arg Arg Pro Pro Met Thr
            500             505             510
Gln Val Tyr Glu Arg Leu Glu Lys Leu Gln Ala Val Val Ala Gly Val
        515             520             525
```

| | | | | | | | | | | | | | | |
|---|---|---|---|---|---|---|---|---|---|---|---|---|---|---|
| Pro | Gly 530 | His | Leu | Glu | Ala | Ala 535 | Ser | Cys | Ile | Pro | Pro 540 | Ser | Pro | Gln | Glu |
| Asn 545 | Ser | Tyr | Val | Ser | Ser 550 | Thr | Gly | Arg | Ala | His 555 | Ser | Gly | Ala | Ala | Pro 560 |
| Trp | Gln | Pro | Leu | Ala 565 | Ala | Pro | Ser | Gly | Ala 570 | Ser | Ala | Gln | Ala | Ala 575 | Glu |
| Gln | Leu | Gln | Arg 580 | Gly | Pro | Asn | Gln | Pro 585 | Val | Glu | Ser | Asp | Glu 590 | Ser | Leu |
| Gly | Gly | Leu 595 | Ser | Ala | Ala | Leu | Arg 600 | Ser | Trp | His | Leu | Thr 605 | Pro | Ser | Cys |
| Pro | Leu 610 | Asp | Pro | Ala | Pro | Leu 615 | Arg | Glu | Ala | Gly | Cys 620 | Pro | Gln | Gly | Asp |
| Thr 625 | Ala | Gly | Glu | Ser | Ser 630 | Trp | Gly | Ser | Gly | Pro 635 | Gly | Ser | Arg | Pro | Thr 640 |
| Ala | Val | Glu | Gly | Leu 645 | Ala | Leu | Gly | Ser | Ser 650 | Ala | Ser | Ser | Ser | Ser 655 | Glu |
| Pro | Pro | Gln | Ile 660 | Ile | Ile | Asn | Pro | Ala 665 | Arg | Gln | Lys | Met | Val 670 | Gln | Lys |
| Leu | Ala | Leu 675 | Tyr | Glu | Asp | Gly | Ala 680 | Leu | Asp | Ser | Leu | Gln 685 | Leu | Leu | Ser |
| Ser | Ser 690 | Ser | Leu | Pro | Gly | Leu 695 | Gly | Leu | Glu | Gln | Asp 700 | Arg | Gln | Gly | Pro |
| Glu 705 | Glu | Ser | Asp | Glu | Phe 710 | Gln | Ser | | | | | | | | |